(12) United States Patent
Carpentier (10) Patent No.: US 11,420,078 B2
(45) Date of Patent: Aug. 23, 2022

(54) IMPLANTABLE ULTRASOUND GENERATING TREATING DEVICE FOR SPINAL CORD AND/OR SPINAL NERVE TREATMENT, APPARATUS COMPRISING SUCH DEVICE AND METHOD

(71) Applicants: SORBONNE UNIVERSITE, Paris (FR); ASSISTANCE PUBLIQUE—HÔPITAUX DE PARIS, Paris (FR)

(72) Inventor: Alexandre Carpentier, Paris (FR)

(73) Assignees: SORBONNE UNIVERSITE, Paris (FR); ASSISTANCE PUBLIQUE—HÔPITAUX DE PARIS, Paris (FR)

( * ) Notice: Subject to any disclaimer, the term of this patent is extended or adjusted under 35 U.S.C. 154(b) by 265 days.

(21) Appl. No.: 16/082,554

(22) PCT Filed: Mar. 11, 2016

(86) PCT No.: PCT/IB2016/000430
§ 371 (c)(1),
(2) Date: Sep. 6, 2018

(87) PCT Pub. No.: WO2017/153798
PCT Pub. Date: Sep. 14, 2017

(65) Prior Publication Data
US 2019/0038923 A1    Feb. 7, 2019

(51) Int. Cl.
*A61N 7/00*    (2006.01)

(52) U.S. Cl.
CPC ........ *A61N 7/00* (2013.01); *A61N 2007/0021* (2013.01); *A61N 2007/0043* (2013.01); *A61N 2007/0047* (2013.01)

(58) Field of Classification Search
CPC .... A61N 2007/0021; A61N 2007/0043; A61N 2007/0047; A61N 7/00
See application file for complete search history.

(56) References Cited

U.S. PATENT DOCUMENTS

| | | |
|---|---|---|
| 1,879,502 A | 9/1932 | Rinman |
| 4,646,756 A | 3/1987 | Watmough et al. |

(Continued)

FOREIGN PATENT DOCUMENTS

| | | |
|---|---|---|
| CN | 101152646 | 4/2008 |
| CN | 103 142 287 | 6/2013 |

(Continued)

*Primary Examiner* — Yi-Shan Yang
*Assistant Examiner* — Alexei Bykhovski
(74) *Attorney, Agent, or Firm* — Clark & Brody LP (57) ABSTRACT

An implantable ultrasound generating treating device (12) to induce spinal cord or spinal nerves treatment, suitable for implantation in the spinal canal and comprises an elongate support member (22, 32) and an array of several treatment transducers (20) distributed along the elongate support member. The several treatment transducers (20) comprise radial transducers emitting an ultrasound treatment beam oriented radially, wherein the treatment transducers (20) have a resonant frequency comprised between 0.5 and 4 MHz. The device has articulating portions so that the implantable device can adapt its shape to a curved elongation path. Also disclosed is an apparatus including the implantable ultrasound generating treating device and methods comprising inserting the implantable ultrasound generating treating device (12) inside the spinal canal of the spine of the patient.

11 Claims, 4 Drawing Sheets

(56) References Cited

U.S. PATENT DOCUMENTS

| | | |
|---|---|---|
| 4,836,191 A | 6/1989 | Noske et al. |
| 5,321,104 A | 6/1994 | Sumino et al. |
| 5,501,655 A | 3/1996 | Rolt et al. |
| 5,524,624 A | 6/1996 | Tepper et al. |
| 5,752,515 A | 5/1998 | Jolesz et al. |
| 6,139,241 A | 10/2000 | Craig et al. |
| 6,254,553 B1 | 7/2001 | Lidgren et al. |
| 6,254,624 B1 | 7/2001 | Oddsen et al. |
| 6,319,241 B1 | 11/2001 | King et al. |
| 6,468,219 B1 | 10/2002 | Njemanze |
| 6,560,486 B1 | 5/2003 | Osorio et al. |
| 6,613,005 B1 | 9/2003 | Friedman et al. |
| 6,666,833 B1 | 12/2003 | Friedman et al. |
| 6,862,479 B1 | 3/2005 | Whitehurst et al. |
| 7,101,337 B2 | 9/2006 | Aubry et al. |
| 7,107,104 B2 | 9/2006 | Keravel et al. |
| 7,211,060 B1* | 5/2007 | Talish ............... A61N 7/00 600/407 |
| 7,522,962 B1 | 4/2009 | Doron et al. |
| 7,575,550 B1 | 8/2009 | Govari |
| 7,878,977 B2 | 2/2011 | Mo et al. |
| 7,896,821 B1 | 3/2011 | Magnin et al. |
| 8,942,781 B2 | 1/2015 | Carpentier et al. |
| 8,977,361 B2 | 3/2015 | Carpentier et al. |
| 9,993,337 B1 | 6/2018 | Brogan et al. |
| 10,076,652 B2 | 9/2018 | Liu et al. |
| 2001/0051819 A1 | 12/2001 | Fischell et al. |
| 2002/0002371 A1 | 1/2002 | Acker et al. |
| 2002/0038086 A1 | 3/2002 | Hynynen et al. |
| 2002/0072741 A1 | 6/2002 | Sliwa et al. |
| 2002/0177792 A1 | 11/2002 | Ooba et al. |
| 2003/0092987 A1 | 5/2003 | Hynynen et al. |
| 2003/0135135 A1 | 7/2003 | Miwa et al. |
| 2003/0195584 A1 | 10/2003 | Dawson |
| 2003/0225331 A1* | 12/2003 | Diederich ............ A61B 18/04 600/437 |
| 2004/0049134 A1* | 3/2004 | Tosaya ............ A61H 23/0236 601/2 |
| 2004/0054282 A1 | 3/2004 | Aubry et al. |
| 2004/0116772 A1 | 6/2004 | Lupin et al. |
| 2004/0122323 A1 | 6/2004 | Vortman et al. |
| 2004/0162507 A1 | 8/2004 | Govari |
| 2005/0020945 A1 | 1/2005 | Tosaya et al. |
| 2005/0021117 A1 | 1/2005 | He et al. |
| 2005/0240170 A1 | 10/2005 | Zhang et al. |
| 2005/0283203 A1 | 12/2005 | Flaherty et al. |
| 2006/0049957 A1 | 3/2006 | Surgenor et al. |
| 2006/0079816 A1 | 4/2006 | Barthe et al. |
| 2006/0129204 A1 | 6/2006 | Pless et al. |
| 2006/0224060 A1 | 10/2006 | Garell et al. |
| 2006/0241529 A1 | 10/2006 | Hynynen et al. |
| 2007/0016041 A1 | 1/2007 | Nita |
| 2007/0038100 A1 | 2/2007 | Nita |
| 2007/0067003 A1 | 3/2007 | Sanchez et al. |
| 2007/0073135 A1 | 3/2007 | Lee et al. |
| 2007/0179558 A1 | 8/2007 | Gliner et al. |
| 2007/0219547 A1 | 9/2007 | Osypka |
| 2007/0225773 A1 | 9/2007 | Shen et al. |
| 2007/0293908 A1 | 12/2007 | Cowan et al. |
| 2008/0004676 A1 | 1/2008 | Osypka et al. |
| 2008/0140149 A1 | 6/2008 | John et al. |
| 2008/0183166 A1 | 7/2008 | Miller |
| 2008/0195160 A1 | 8/2008 | Wingeier et al. |
| 2008/0221490 A1 | 9/2008 | Zahos |
| 2008/0249409 A1 | 10/2008 | Fraser et al. |
| 2008/0275526 A1 | 11/2008 | Lozano |
| 2008/0287837 A1 | 11/2008 | Makin et al. |
| 2008/0319355 A1 | 12/2008 | Nita |
| 2008/0319375 A1 | 12/2008 | Hardy |
| 2009/0005711 A1 | 1/2009 | Konofagou et al. |
| 2009/0082860 A1 | 3/2009 | Schieber et al. |
| 2009/0093724 A1 | 4/2009 | Pernot et al. |
| 2009/0112278 A1 | 4/2009 | Wingeier et al. |
| 2009/0112280 A1 | 4/2009 | Wingeier et al. |
| 2009/0149781 A1 | 6/2009 | Liu et al. |
| 2009/0238763 A1 | 9/2009 | Yu et al. |
| 2009/0248165 A1 | 10/2009 | Lin et al. |
| 2009/0254134 A1 | 10/2009 | Nikolov et al. |
| 2010/0010394 A1 | 1/2010 | Liu et al. |
| 2010/0041988 A1 | 2/2010 | Pijnenburg et al. |
| 2010/0056924 A1 | 3/2010 | Powers |
| 2010/0137937 A1 | 6/2010 | John et al. |
| 2010/0143241 A1 | 6/2010 | Johnson et al. |
| 2010/0145414 A1 | 6/2010 | Decre et al. |
| 2010/0160779 A1 | 6/2010 | Browning et al. |
| 2010/0217160 A1 | 8/2010 | Saguchi et al. |
| 2010/0222715 A1 | 9/2010 | Nita |
| 2010/0224950 A1 | 9/2010 | Dinyari et al. |
| 2010/0249597 A1 | 9/2010 | Shi |
| 2010/0268088 A1 | 10/2010 | Prus et al. |
| 2011/0040172 A1 | 2/2011 | Carpentier et al. |
| 2011/0046694 A1 | 2/2011 | Forsell |
| 2011/0051554 A1 | 3/2011 | Varray et al. |
| 2011/0089160 A1 | 4/2011 | Kuriki |
| 2011/0112394 A1 | 5/2011 | Mishelevich |
| 2011/0178441 A1 | 7/2011 | Tyler |
| 2011/0178442 A1 | 7/2011 | Mishelevich |
| 2011/0208095 A1 | 8/2011 | Jolesz et al. |
| 2011/0213200 A1 | 9/2011 | Mishelevich |
| 2011/0245734 A1 | 10/2011 | Wagner et al. |
| 2011/0295105 A1 | 12/2011 | Konofagou et al. |
| 2012/0010711 A1 | 1/2012 | Antonyshyn et al. |
| 2012/0046531 A1 | 2/2012 | Hua |
| 2012/0065458 A1 | 3/2012 | Tol |
| 2012/0078140 A1 | 3/2012 | Nita |
| 2012/0083719 A1 | 4/2012 | Mishelevich |
| 2012/0109019 A1 | 5/2012 | Schneider et al. |
| 2012/0123270 A1 | 5/2012 | Klee et al. |
| 2012/0130288 A1* | 5/2012 | Holland ............... A61N 7/00 601/2 |
| 2012/0143058 A1 | 6/2012 | Powers et al. |
| 2012/0172949 A1 | 7/2012 | Wagenaar Cacciola et al. |
| 2012/0203079 A1 | 8/2012 | McLaughlin |
| 2012/0277639 A1 | 11/2012 | Pollock et al. |
| 2012/0283502 A1 | 11/2012 | Mishelevich |
| 2012/0323147 A1 | 12/2012 | Scheirer et al. |
| 2013/0006106 A1 | 1/2013 | O'Reilly et al. |
| 2013/0046229 A1 | 2/2013 | Konofagou et al. |
| 2013/0049534 A1 | 2/2013 | Clark et al. |
| 2013/0079682 A1 | 3/2013 | Mishelevich |
| 2013/0131754 A1 | 5/2013 | Sarvazyan |
| 2013/0178764 A1 | 7/2013 | Eckhouse et al. |
| 2013/0178765 A1 | 7/2013 | Mishelevich |
| 2013/0204316 A1* | 8/2013 | Carpentier ............ A61B 8/0816 607/45 |
| 2013/0251633 A1 | 9/2013 | Borden et al. |
| 2013/0281890 A1 | 10/2013 | Mishelevich |
| 2013/0324891 A1 | 12/2013 | Towe |
| 2013/0324892 A1 | 12/2013 | Zhu et al. |
| 2013/0331685 A1 | 12/2013 | Liu et al. |
| 2013/0338526 A1 | 12/2013 | Howard |
| 2014/0005521 A1 | 1/2014 | Kohler et al. |
| 2014/0074076 A1 | 3/2014 | Gertner |
| 2014/0114216 A1 | 4/2014 | Konofagou et al. |
| 2014/0249454 A1 | 9/2014 | Carpentier |
| 2014/0296646 A1 | 10/2014 | Wingeier et al. |
| 2014/0330123 A1 | 11/2014 | Manwaring et al. |
| 2015/0005614 A1 | 1/2015 | Heggeness et al. |
| 2015/0005680 A1* | 1/2015 | Lipani ............... A61B 18/20 601/15 |
| 2015/0045724 A1 | 2/2015 | Chen et al. |
| 2015/0065871 A1 | 3/2015 | Konofagou et al. |
| 2015/0148710 A1 | 5/2015 | Towe et al. |
| 2015/0224345 A1 | 8/2015 | Warlick |
| 2015/0231417 A1 | 8/2015 | Metcalf et al. |
| 2015/0265305 A1* | 9/2015 | Stulen ............... A61F 7/00 606/169 |
| 2015/0297176 A1 | 10/2015 | Rincker et al. |
| 2016/0000411 A1 | 1/2016 | Raju et al. |
| 2016/0001096 A1 | 1/2016 | Mishelevich |
| 2016/0016012 A1 | 1/2016 | Youn et al. |
| 2016/0107002 A1 | 4/2016 | Nita |
| 2016/0151618 A1* | 6/2016 | Powers ............... A61B 8/4209 600/439 |

(56) References Cited

U.S. PATENT DOCUMENTS

| | | | |
|---|---|---|---|
| 2016/0184614 A1 | 6/2016 | Matula et al. | |
| 2016/0242648 A1 | 8/2016 | Konofagou et al. | |
| 2016/0338663 A1 | 11/2016 | Chen et al. | |
| 2017/0080255 A1* | 3/2017 | Law | B06B 1/0622 |
| 2018/0263602 A1 | 9/2018 | Elvira Seguro et al. | |
| 2018/0353777 A1 | 12/2018 | Dianis et al. | |
| 2021/0106849 A1 | 4/2021 | Liu et al. | |

FOREIGN PATENT DOCUMENTS

| | | |
|---|---|---|
| DE | 3150513 | 6/1983 |
| DE | 19 641 935 | 9/1997 |
| DE | 10 2010 001020 | 7/2011 |
| EP | 0 643 982 | 3/1995 |
| EP | 0 701 840 | 3/1996 |
| EP | 1 262 160 | 12/2002 |
| EP | 1 312 423 | 5/2003 |
| EP | 1 774 989 | 4/2007 |
| EP | 1 806 238 | 7/2007 |
| EP | 1 834 646 | 9/2007 |
| GB | 2 445 585 | 7/2008 |
| GB | 2 473 265 | 3/2011 |
| GR | 20070100349 | 1/2009 |
| JP | 60-75809 | 4/1985 |
| JP | 05-68684 | 3/1993 |
| JP | 2001-327495 | 11/2001 |
| JP | 2003-325616 | 11/2003 |
| JP | 2007-289715 | 11/2007 |
| WO | 92/12605 | 7/1992 |
| WO | 92/22350 | 12/1992 |
| WO | 96/39079 | 12/1996 |
| WO | 98/47569 | 10/1998 |
| WO | 99/34758 | 7/1999 |
| WO | 00/78232 | 12/2000 |
| WO | 01/09111 | 2/2001 |
| WO | 02/100480 | 12/2002 |
| WO | 03/059437 | 7/2003 |
| WO | 03/061756 | 7/2003 |
| WO | 2004/050175 | 6/2004 |
| WO | 2004/093725 | 11/2004 |
| WO | 2004/105640 | 12/2004 |
| WO | 2005/009244 | 2/2005 |
| WO | 2005/065738 | 7/2005 |
| WO | 2006/092061 | 9/2006 |
| WO | 2006/105463 | 10/2006 |
| WO | 2006/130445 | 12/2006 |
| WO | 2006/138702 | 12/2006 |
| WO | 2007/064453 | 6/2007 |
| WO | 2007/121133 | 10/2007 |
| WO | 2007/124458 | 11/2007 |
| WO | 2008/072125 | 6/2008 |
| WO | 2009/029141 | 3/2009 |
| WO | 2009/067323 | 5/2009 |
| WO | 2009/111317 | 9/2009 |
| WO | 2009/115523 | 9/2009 |
| WO | 2009/132855 | 11/2009 |
| WO | 2010/009141 | 1/2010 |
| WO | 2011/029208 | 3/2011 |
| WO | 2011/079177 | 6/2011 |
| WO | 2011/101039 | 8/2011 |
| WO | 2011/101492 | 8/2011 |
| WO | 2011/103098 | 8/2011 |
| WO | 2012/030522 | 3/2012 |
| WO | 2012/125172 | 9/2012 |
| WO | 2013/048912 | 4/2013 |
| WO | 2013/177430 | 11/2013 |
| WO | 2014/013285 | 1/2014 |
| WO | 2014/060914 | 4/2014 |
| WO | 2014/207666 | 12/2014 |
| WO | 2016/047103 | 4/2015 |
| WO | 2015/075603 | 5/2015 |
| WO | 2015/079324 | 6/2015 |

\* cited by examiner

IMPLANTABLE ULTRASOUND GENERATING TREATING DEVICE FOR SPINAL CORD AND/OR SPINAL NERVE TREATMENT, APPARATUS COMPRISING SUCH DEVICE AND METHOD

TECHNICAL FIELD

The present invention relates to a device, an apparatus and a method for the treatment of spinal cord and or spinal nerve(s) disorders, especially for the transient disruption of the blood-spinal cord barrier and/or of the blood-spinal nerve barrier of a vertebrate subject, especially of a human.

BACKGROUND ART

The spinal cord and/or the spinal nerve(s) may to subject to various physiological disorders which induce different forms of pathologies There is a clear need for improving therapies in this domain. Also, there is a need to improve the repair and/or rehabilitation treatments of the spinal cord and/or spinal nerve(s), for example for hemiplegia and paraplegia, including with cell transplant and/or stem cell regeneration.

Some available treatments include action of drugs on the spinal cord and/or spinal nerve tissues. However, the blood-spinal cord barrier (hereinafter BSCB) limits or prevents the penetration of therapeutic drugs in the spinal cord or nerve tissues. Similarly, the blood-spinal nerve barrier (hereinafter BSNB) prevents the penetration of therapeutic drugs in the spinal cord or nerve tissues.

It is known to use spinal drug delivery catheters inserted in the spinal canal, but this only allows injection of a fluid which only penetrates to a limited and insufficient extent into spinal cord or spinal nerve tissues.

Some documents suggest the use of spinal cord electrical stimulation, sometimes in association with drug delivery. U.S. Pat. No. 6,319,241 describes techniques for positioning therapy delivery elements within a spinal cord or a brain to provide electrical stimulation and/or drug infusion to a precise target. U.S. Pat. No. 6,862,479 describes implantable system control units (SCU) to apply one or more stimulating drugs and/or electrical pulses to a spinal section responsible for innervating the male reproductive organs. Such methods do not cause any significant opening of the blood spinal cord barrier.

WO-96/39079 describes a method and an apparatus for performing ultrasonic imaging of a region of a patient while simultaneously applying therapeutic ultrasonic waves to the region for rupturing vesicles administered to that region, for purposes such as enhanced cavitation or the targeted release of a bioactive agent contained in the vesicles into the region.

Many systems and methods have been disclosed which rely on high energy ultrasounds for causing an intended damage to the targeted tissue. US-2005/0240170 describes methods and systems for producing hemostasis, tissue closure, or vessel closure by inserting a thermal delivery probe into a passageway and emitting thermal energy from the probe to produce the hemostasis or tissue closure. The thermal delivery probe may have one or more ultrasound transducers positioned in an elongated shaft. GR20070100349 discloses an ultrasound diathermy system that can be applied to the spinal cord. It causes a cut and hemostasis in the tissues, it seals vessels of relatively small transection without causing their rupture.

US-200810287837 discloses an interstitial end effector which is interstitially insertable into patient tissue, which includes at least one medical-treatment ultrasound transducer, and which includes at least one end-effector-tissue-track ablation device. US-2007/073135, describes an integrated ultrasound imaging and ablation probe. EP-1774989 discloses an ultrasound probe which comprises one or more transducers positionable on, in proximity to or within a cancerous mass of tissue. The one or more transducers are capable of delivering sufficient levels of acoustic energy to (a) induce coagulative necrosis of a region of the tissue surrounding the transducer, and (b) induce sonoporation of a chemotherapy agent into cancer cells in the tumor and in the margins of tissue adjacent the necrosis region of tissue. EP-0643982 describes an ultrasound thermotherapy probe and method for treatment of prostate tissues. WO-2007/124458 describes a method of thermal treatment for myolysis and destruction of benign uterine tumors. JP-2007-289715 describes an ultrasonic diagnostic and therapeutic system in which high density ultrasonic energy can be concentrated and accurately irradiated on a desired position of a location to be treated.

WO-03/059437 describes a system and method for providing directional ultrasound therapy to skeletal joints, such as spinal joints. WO-03061756 describes a long-term implantable ultrasound therapy system and method is provided that provides directional, focused ultrasound to localized regions of tissue within body joints, such as spinal joints. US-2016/0016012 discloses an external stimulation apparatus using low intensity focused ultrasound, which has a low intensity ultrasound focusing array having a plurality of transducers for outputting low intensity ultrasound beams, and a fixing device to which the low intensity ultrasound focusing array is attached, the fixing device being configured to fix the low intensity ultrasound focusing array to an upper body of a user.

US-2015/0224345 discloses a method of treating a patient having a nerve injury or spinal cord injury or spinal cord lesions, comprising the steps of: activating an acoustic shock wave generator or source to emit acoustic shock waves from a shock wave head; and administering an effective exposure of acoustic shock waves in a pulse or wave pattern having a low energy density less than 1.0 mJ/mm2 per shock wave directly onto a treatment zone in a region extending from the medulla oblongata in the lower brain stem to the lower end of the spinal cord.

US-2005/0020945 discloses an apparatus including an emitter means to deliver acoustic, ultrasonic or vibratory energy in, into or from within a region of the patient's brain or spine which contains or is transportably-coupled to cerebrospinal fluid (CSF) or blood capable of bearing or bearing a chemical or biological species, reactant, fragment or byproduct of the disease.

U.S. Pat. No. 8,942,781 describes a percutaneous probe, made in MRI-compatible materials, having: a body percutaneously inserted into the tissue of a patient's body organ having a region to be analyzed, treated and monitored during a single medical procedure; at least one information collection sensing device, treatment application transducers organized in a 360° fashion to emit focused or defocused therapeutic ultra-sound waves.

U.S. Pat. No. 8,977,361 describes an apparatus for the treatment of a brain affection, which comprises at least one implantable generator made of non-ferromagnetic material comprising a casing, and an ultrasound generating treating device positioned into said casing to induce brain affection treatment by emission of ultrasound waves.

US-2015/0231417 discloses a method for treating a spine comprising the steps of: providing a magnetic resonance imaging (MRI) device;

identifying a surgical site for treatment of a spinal disorder with the MRI device, the surgical site including a portion of a spine; providing a high intensity focused ultrasound (HIFU) device including a transducer for emitting ultrasound energy; determining parameters of treatment for the surgical site; and applying a dosage of ultrasound energy to the surgical site with the HIFU device for treating the disorder.

US-2013/0178765, US-2013/0281890 and US-2016/0001096 describe methods and systems for non-invasive neuromodulation of the spinal cord utilizing a transducer to deliver pulsed ultrasound energy to up regulate or down regulate neural targets for the treatment of pain and other disease conditions.

There remains the need for a system and a method capable of causing the transient disruption of the blood-spinal cord barrier and/or of the blood-spinal nerve barrier of a vertebrate subject. The specificity of these tissues and their location within the spine vertebrae, especially in the spinal canal, and the need to cause only a transient disruption of the blood-spinal cord barrier and/or of the blood-spinal nerve barrier in the targeted tissues, without damaging the targeted tissues, require a specific system and a specific method not yet available from the prior art.

SUMMARY

The invention relates to an implantable ultrasound generating treating device to induce spinal cord or spinal nerves treatment by emission of ultrasound waves, wherein the ultrasound generating treating device is suitable for implantation in the spinal canal and comprises:
  an elongate support member extending along an elongation path;
  an array of several ultrasound generating treatment transducers distributed along the elongate support member along an active portion on the elongation path The several treatment transducers comprise preferably radial transducers, each radial treatment transducer emitting an ultrasound treatment beam oriented radially with respect to the elongation path over an effective angular range of at least 120°, preferably at least 180°, and most preferably of 360° around the elongation path at the location of the radial transducer.

The treatment transducers preferably have an ultrasound generating resonant frequency comprised between 0.5 and 4 MHz The implantable device preferably has articulating portions along the active portion of the elongation path so that the active portion of the implantable device can adapt its shape to a curved elongation path.

According to other optional features of such implantable device, taken alone or in combination:
  The articulating portions may comprise comparatively more flexible portions of the device in between of comparatively more rigid portions.
  The comparatively more rigid portions may correspond to the location of the treatment transducers along the elongation path.
  The device may comprise an elongate outer sheath tube containing the ultrasound generating treatment transducers.
  The elongate outer sheath tube may be made of a silicone, polyurethane, and/or polytetrafluorethylene based material.
  The elongate outer sheath tube may form at least part of the elongate support member.
  The radial treatment ultrasound generating transducers may be cylindrical, with an axis parallel to the elongation path.
  The radial treatment transducers may be tubular, with an axis parallel to the elongation path, and with a central aperture extending along their axis.
  The elongate support member may comprise an internal support member extending though the central aperture of the treatment transducers.
  The ultrasound generating treating device may comprise ultrasonic monitoring transducers.
  The treatment transducers may be connectable by an electrical connection circuit to a generator delivering electric drive signals driving the generation of ultrasound from the treatment transducers.
  The electrical connection circuit of the implantable device may start from an implantable connection receiver of the implantable device and may deliver electric signals to the treatment transducers for driving the ultrasound generation of the treatment transducers.
  The connection receiver may be designed for cooperation with an external electrical generator to achieve electrical connection between the generator and the ultrasound generating treating device.
  The connection receiver may be designed for cooperation with a connector of the generator which may comprise one or several transdermal needles suitable for plugging into the connection receiver through the patient's skin.
  The device may comprise an implantable electrical generator.
  The implantable generator may be remotely controlled by an external controller.

The invention also relates to an apparatus to induce spinal cord or spinal nerves treatment by emission of ultrasound waves, comprising:
  an implantable ultrasound generating treating device having any of the preceding features;
  an electrical generator which generates electric signals to be delivered to the transducers of the implantable ultrasound generating treating device;
  a controller.

The invention also relates to a method for transiently opening the blood-spinal cord barrier and/or blood-spinal nerve barrier in at least one treatment zone of the spinal cord or spinal nerve(s) of a vertebrate patient, especially of a human patient, said method comprising the application to the treatment zone of the spinal cord and/or spinal nerve(s) of the patient of at least one ultrasound treatment beam, wherein the method comprises the insertion of an implantable ultrasound generating treating device) inside the spinal canal of the spine of the patient and the generation of least one ultrasound treatment beam.

According to other optional features of such method, taken alone or in combination:
  The implantable ultrasound generating treating device may be implanted in the subdural and/or in the epidural space of the spinal canal.
  The treatment zone may extends throughout the extension of several vertebrae of the patient, and the method may comprise the insertion of an elongate implantable ultrasound generating treating device inside the spinal canal of the spine and the generation of least one ultrasound treatment beam.

The method may involve the injection of an ultrasound contrast agent in the patient's blood circulation system, prior to and/or during the generation of the least one ultrasound treatment beam.

The ultrasound treatment beam may have a resonant frequency ranging from 0.5 to 4 MHz, preferably ranging from 0.75 to 2 MHz.

The pressure level of the ultrasound treatment beam may be comprised between 0.8 MPa and 3.0 Mpa.

The applied ultrasound treatment beam may have a mechanical index (MI) of approximately from 0.3 to 3.00.

The ultrasound treatment beam may be a pulsed beam.

The implantable ultrasound generating treating device may have one or several of the features above.

BRIEF DESCRIPTION OF THE DRAWINGS

The device, apparatus and method of the present invention will be further described in detail below with reference to the accompanying drawings showing preferred embodiments of the apparatus of the invention.

In the figures.

DETAILED DESCRIPTION

Figure 1:
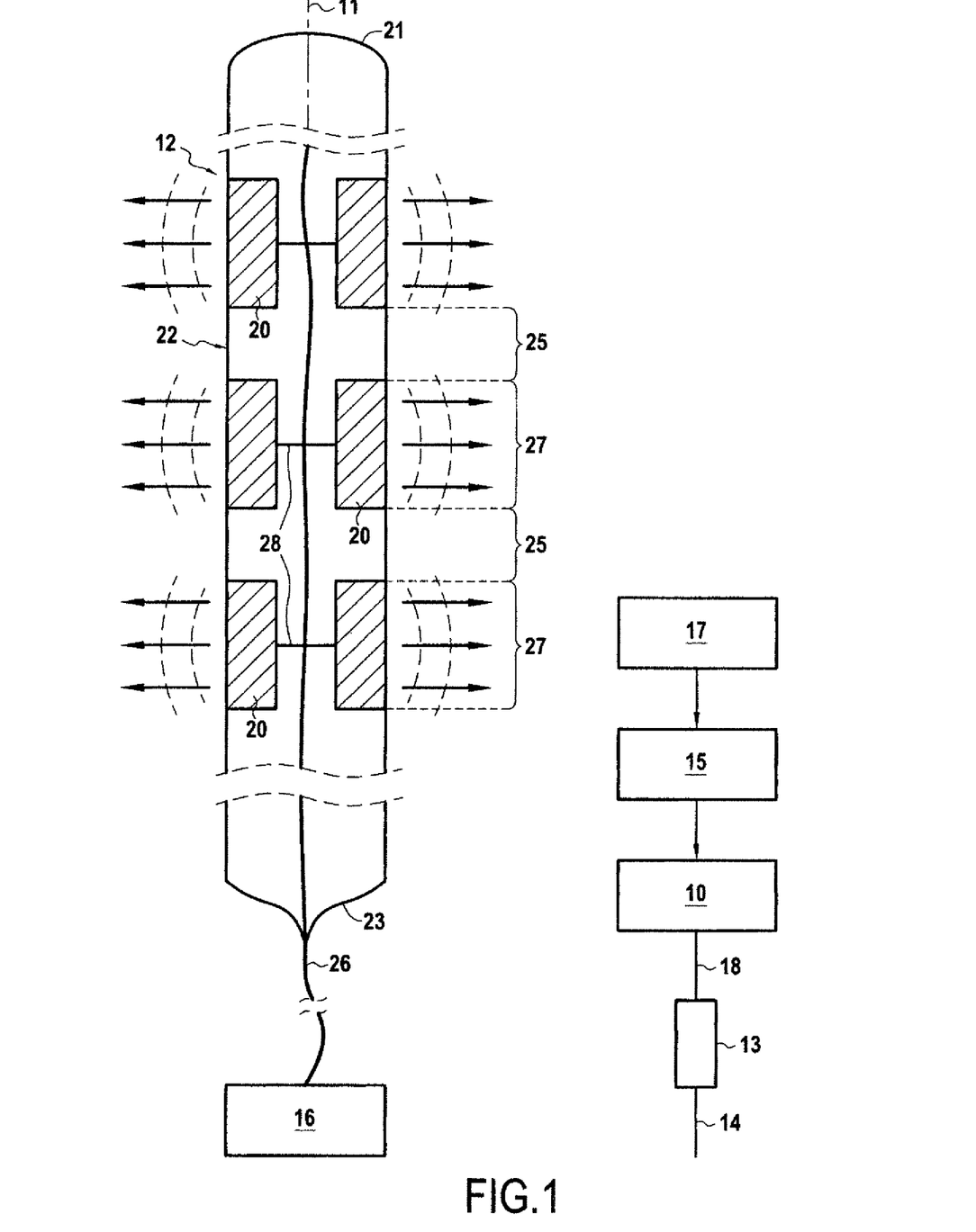
FIG. 1 represents schematically a first embodiment of the apparatus of the present invention.

On FIG. 1 are shown the main components of an apparatus to induce spinal cord or spinal nerves treatment by emission of ultrasound waves, comprising an exemplary embodiment of an implantable ultrasound generating treating device 12 according to the invention.

The apparatus comprises:
an implantable ultrasound generating treating device 12;
an electrical generator 10 which generates electric signals to be delivered to the transducers of the implantable ultrasound generating treating device;
a controller 15 to set and control the working parameters of the generator.

According to an aspect of the invention, the implantable ultrasound generating treating device 12 is suitable for implantation inside the spinal canal of the spine of a patient who is awaiting the receipt of, or is receiving medical care or was/is/will be the object of a medical procedure, or is monitored for the diagnosis or the development of a disease. The patient can be any vertebrate subject, especially a mammal and in particular a human i.e., a person of the species Homo sapiens.

Figure 2:
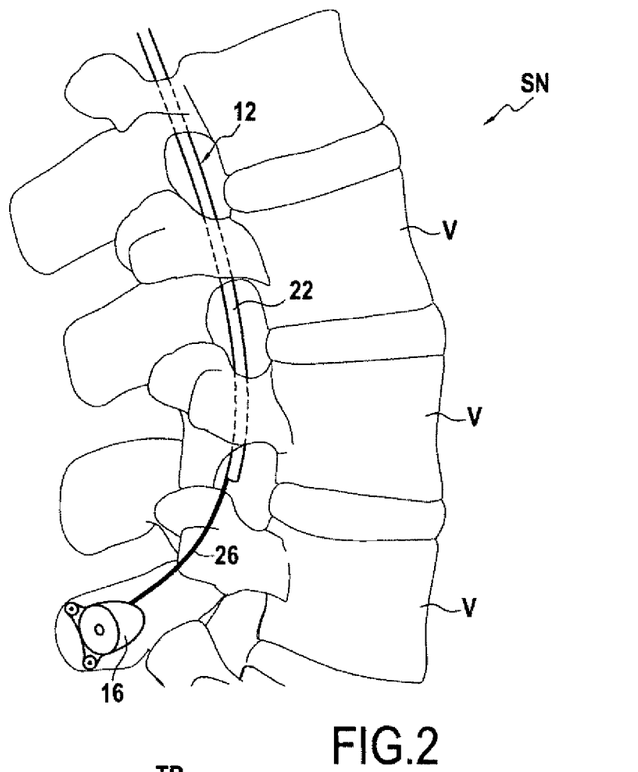
FIGS. 2 and 3 represent schematically an example of the implantation of a device according to the invention in the spinal canal of patient, respectively in a sagittal plane and in a transversal plane of the patient.
Figure 3:
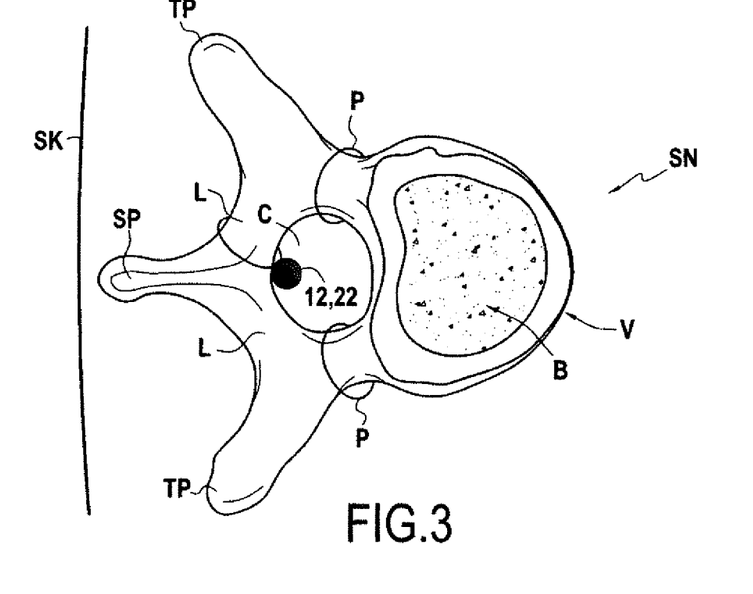

FIGS. 2 and 3 illustrate schematically such an implantation in the case of a human patient. On those figures, one can see the spine SN of the patient, on the internal side of the skin SK of the back of the patient. The spine SN comprises vertebrae V. In a typical human vertebra, as shown on FIG. 3 in a transverse cross-section perpendicular to the extension of the spine, a vertebra comprises a spinal canal SC portion which is delimited:
towards the front by the vertebra body B,
towards the sides by the two pedicles P which join the body B to the two transverse process TP, and
towards the rear by the spinous process SP and the two laminas L which join each the spinal process SP to one of the two transverse processes TP.

The spinal cord C is located in the spinal canal and the spinal nerves (not represented) emerge from the spinal cord and extend laterally out of the spinal canal between two vertebrae.

More particularly, the implantable ultrasound generating treating device 12 is suitable for implantation in the subdural and/or in the epidural space of the spinal canal.

In some embodiments, the generator 10 can be implantable inside the body of the patient. Such an implantable generator can be remotely controlled by an external controller, preferably through wireless communication.

In other embodiments, as shown on FIGS. 1 and 2, the generator 10 is external to the body.

In operation, the generator 10 and the implantable ultrasound generating treating device 12 are to be connected electrically. Whereas such electrical connection could be achieved without contact, such as by inductive coupling, the electrical connection of the shown example is a more conventional cable connection. Such electrical connection could be permanent. However, in the shown embodiment of the invention, electrical connection is preferably achieved through a connector device 13 of the generator system 10 and a connection receiver 16 of the implantable device 12 which can be connected and disconnected. In the shown embodiment, the connector device 13 and the connection receiver 16 may be physically coupled to achieve electrical connection and may be decoupled without the need to remove the implantable device 12 from the body of the patient. In this example, the connection receiver 16 forms a socket of a plug-and-socket connection, while the connector device 13 forms the plug of a plug-and-socket connection. The connection receiver 16 is thus designed for cooperation with the external electrical generator 10 to achieve electrical connection between the generator 10 and the ultrasound generating treating device 12.

In the shown embodiment of FIG. 2, the connection receiver 16 is implantable. It may be affixed, as shown, onto a vertebra, for example on the spinous process or a lamina of the vertebra. The connection receiver 16 can thus be located below the skin which covers the spine.

The connector device 13 may thus be connected to generator 10 by a cable 18 having a suitable length, for example at least 50 centimetres long, preferably more than one meter.

The implantable ultrasound generating treating device 12 is suitable for implantation in the spinal canal and comprises:
an elongate support member 22, 32 extending along an elongation path 11,
an array of several ultrasound generating treatment transducers 20 distributed along the elongate support member 22, 32 along an active portion of the device on the elongation path 11.

The support member maintains a set distance between the ultrasound generating treatments transducers 20 along the elongation path, preferably preventing both an increase and a decrease of the distance between the ultrasound generating treatments transducers 20 along the elongation path. The active portion of the device is the portion of the device 12 along which the treatment transducers 20 are arranged.

A support member can be for example in the form of tube, of a column, of a grid, of a skeleton, etc. . . .

In itself, the support member may have a constant flexibility along its length, or could have segments of different flexibility.

The support member can comprise several members extending in parallel along all or part of the active portion, including extending coaxially. In case of multiple parallel members, the members can be connected directly or through the treatment transducers 20.

The support member can comprise several parts along its length, for example in view of providing a modular construction which can be easily constructed to the adequate length along the elongation axis.

As described hereunder, the implantable ultrasound generating treating device 12 may additionally comprise an electrical connection network with one or several electrically independent electric connection circuits 24.

In the shown embodiment, the implantable ultrasound generating treating device 12 comprises an elongate tube 22 which primarily forms a protective outer sheath for the transducers. It encapsulates an internal space of the implantable device in which the transducers are located, preferably in a watertight fashion with respect to the exterior of the tube. The elongate tube is thus preferably closed at its both ends 21, 23 along the elongation path 11.

In use, the elongate tube 22 is meant to be in contact with body fluids and tissues of the patient, so it is preferably made of biocompatible material, such as a silicone, polyurethane, and/or polytetrafluoroethylene based material. The elongate tube 22 may have several layers of material, possibly of different composition.

The elongate tube 22 is preferably made of one single part, for example obtained by extrusion. However, a multi-part construction is also possible, for example in view of providing a modular construction which can be easily constructed to the adequate length along the elongation axis.

In some embodiments, as shown on FIG. 1, the tube 22 may serve also as a support member for the treatment transducers 20, the treatment transducers 20 being thus affixed to the elongate tube 22.

The elongate tube 22 in itself may have a constant rigidity along its length, or could have segments of different rigidity.

Figure 5:
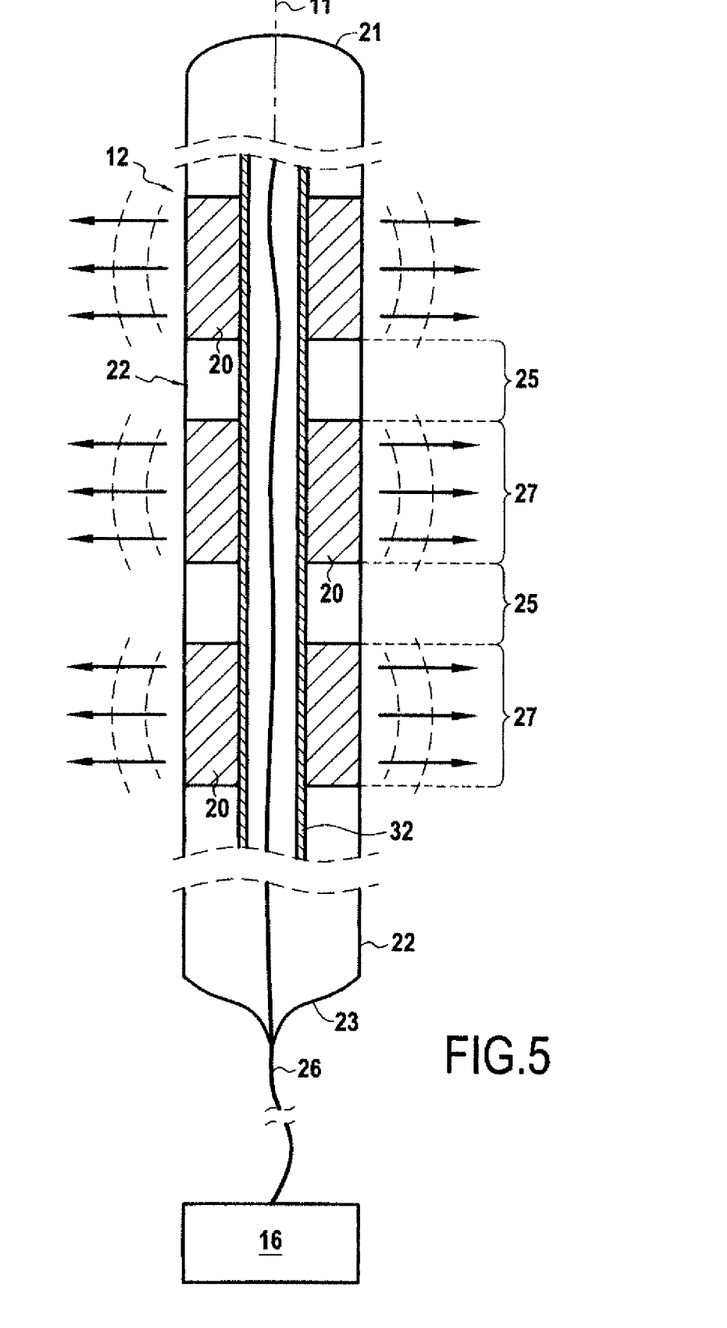
FIG. 5 represents schematically a variant of an implantable ultrasound generating device of the present invention.

However, in some embodiments, as shown on FIG. 5, the support member could comprise a distinct support member 32, distinct from a tubular outer protective sheath, the treatment transducers 20 being thus affixed to the distinct support member 32.

As shown on FIG. 5, in those embodiments having a support member 32 distinct from an outer protective sheath, which may be formed by an elongate tube 22 as described above, the outer protective sheath may also have a role of supporting the treatment transducers 20, in which case the support member can comprise both a distinct support member 32 and an outer protective sheath such as the elongate tube 22.

The several ultrasound treatment transducers 22 comprise radial transducers, each radial treatment transducer emitting an ultrasound beam oriented radially with respect to the elongation path 11, i.e. perpendicularly to the elongation path, over an effective angular range of at least 120°, preferably over 180° and more preferably over 360° around the elongation path at the location of the radial transducer.

Preferably, the ultrasound treatment beam delivered by a given radial treatment transducer 20 has propagation directions contained in a plane which is perpendicular to the elongation axis at the location of the transducer 20 or which deviate from this plane by an angle less than 45°, preferably less than 30°, considering only those propagation directions for which acoustic pressure of the ultrasound field is equal to at least a certain percentage, for example 25%, of the acoustic pressure at the same distance from the elongation axis along a direction of maximum acoustic pressure.

The effective angular range of the radially oriented ultrasound beam is the angle, in a plane perpendicular to the elongation path at the location of the radial transducer, containing the propagation directions for which acoustic pressure of the ultrasound field is equal to at least a certain percentage, for example 25%, preferably at least 50%, more preferably at least 75% of the acoustic pressure along a direction of maximum acoustic pressure in that plane.

Preferably, the effective angular range is a continuous range.

Thus, in a plane perpendicular to the elongation path at the location of the radial transducer, the acoustic power is not necessarily constant in all directions around the elongation axis contained in the effective angular range. However, the acoustic pressure delivered in the effective angular range is considered sufficient in all directions of the effective angular range to achieve the desired therapeutic effect of transiently opening the BSCB or BSNB.

The radial treatment ultrasound generating transducers may be cylindrical, with an axis parallel to the elongation path 11.

The radial ultrasound treatment transducers may be tubular, with an axis parallel to the elongation path 11, and with a central aperture extending along their axis. In such a case the elongate support member may, as shown in FIG. 5, comprise an internal support member extending through the central aperture of the ultrasound treatment transducers. However, even in the case of tubular ultrasound treatment transducers, the support member may be external to the ultrasound treatment transducers. In both cases, the central aperture of the transducers may still serve as a pathway for the electrical connection circuit 24.

Cylindrical or tubular radial transducers could exhibit a cross section where the outer surface, i.e. the ultrasound emitting surface, is in the shape of, or aligned along a line which can be a circle, or a part thereof such as a semi-circle, an ellipse or quasi ellipse or part thereof, a parabola or quasi parabola or part thereof, an hyperbola or quasi hyperbola or part thereof, or any curved or prismatic line, as long as the emitted ultrasound treatment beam is oriented radially as defined above.

The elongation axis at the location of transducer can be the axis of the transducer cylinder.

A radial treatment transducer 20 can be made of a single transducer element, but is preferably made of several transducer elements which are arranged around the elongation axis along the effective angular range.

Figure 4:
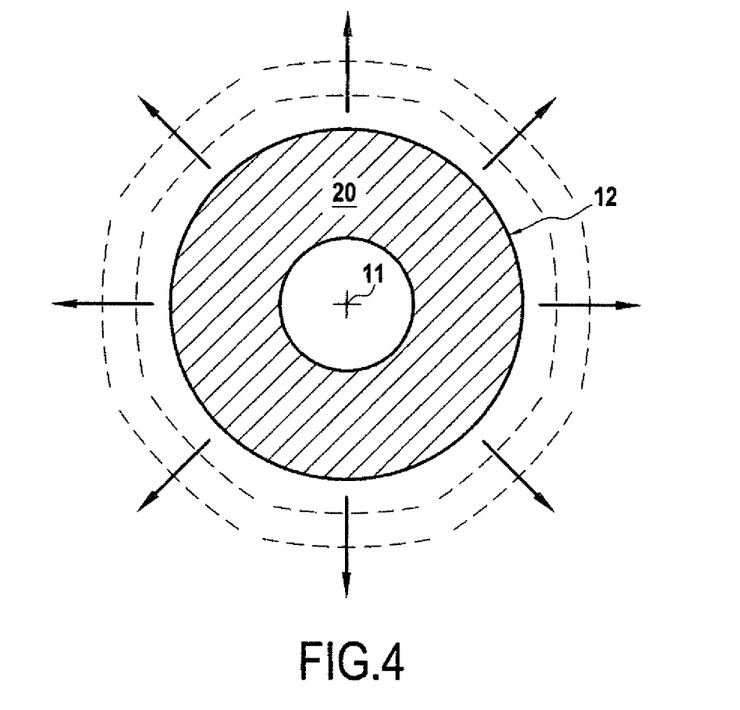
FIG. 4 represents schematically a cross section of the implantable device, along a plane perpendicular to the elongation path, through a treatment transducer, showing the radial propagation directions of the ultrasound treatment beam.

In FIG. 4, it is shown an example where a radial treatment transducer 20 has, in a plane perpendicular to the elongation path at the location of the radial transducer, eight principal directions of propagation along which the acoustic power reaches locally a maximum level at a same given distance from the elongation axis along that direction. These eight maximum levels are preferably in the same order of magnitude, preferably not different by more than 25%. These eight principal directions of propagation are spread over 360°, at regular intervals. Such radial transducer can typically be made of eight transducer elements. Another example could have the same features for more principal directions, for example for at least 10, 15, 20 or 30 principal directions. Having an effective angular range of at least 120°, preferably over 180°, allows that, if the implantable device 12 is correctly installed in the subdural and/or in the epidural space of the spinal canal, the spinal cord will be effectively treated.

Having an effective angular range of 360°, allows that once the implantable device 12 is installed in the spinal canal, the spinal cord will be effectively treated no matter what is the effective angular orientation of the implantable device 12 around its axis.

A radial treatment transducer 20 may have a longitudinal extension, along the direction of the elongation path, which may be comprised between 1 and 20 mm, preferably comprised between 3 and 10 mm.

The ultrasound generating treatment transducers 20 are preferably chosen into the group formed by piezo-composite elements, piezo-ceramic elements, CMUT elements (Capacitive micro-machined ultrasonic transducers), or PVDF elements (Poly(vinylidene fluoride)). Piezo-composite elements or piezo-ceramic elements usually have a size in the range of 1 to 50 mm in diameter. CMUT elements usually have a size in the range of 10 to 50 µm in diameter. Piezoelectric components are commonly used in the medical field as ultrasound transducers. A given transducer can comprise one or several discrete elements which are activated simultaneously.

Preferably, the treatment transducers generate unfocused ultrasounds.

The ultrasound treatment transducers have an ultrasound generating resonant frequency comprised between 0.5 and 4 MHz, more preferably between 0.75 and 2 MHz, for achieving transient disruption of the blood-spinal cord barrier and/or of the blood-spinal nerve barrier of the targeted portion of the spinal cord and/or spinal nerve(s).

In most commonly used ultrasound generating transducers 20, the ultrasound energy is generated by virtue of the vibration created in the core of the transducer by an alternating voltage by virtue of a piezoelectric effect or capacitive variation. The transducer is fed with an electric voltage which may have a given frequency or which may have a frequency spectrum which may be decomposed into preferably a limited number of main frequencies. The core of the transducer may thus be designed such that it exhibits at least one inherent resonant frequency.

A resonant frequency of the transducer can be defined as the frequency of the drive signal for which the ratio of the acoustic power output divided by consumed electrical power reaches a maximum (at least within neighbouring frequencies). For a typical piezoceramic transducer, this ratio is typically between 50% and 90% at a resonant frequency. If the electric current fed to the transducer exhibits such frequency, it will induce in the transducer a resonant vibration which will generate ultrasound. If the electric current fed to the transducer exhibits only a frequency or frequencies which lie outside of a resonant range around the resonant frequency, then the acoustic power output will be less than 25% of the power delivered when driven with a given voltage at its resonant frequency.

It must be noted that the term resonant frequency, as used in this text, covers an individual peak resonant frequency, at which the transducer 20 delivers a peak ultrasound field power/intensity for a given electric drive signal power, or a resonant frequency range, around such peak resonant frequency, for which the transducer 20 delivers a ultrasound field power/intensity higher than a minimum field power/intensity, which may be expressed as a percentage of the peak ultrasound field power/intensity.

A transducer may have a given operating frequency by choosing for example its resonant thickness along a given direction along which the ultrasound waves are to be emitted. For example, thickness for a 1 MHz transducer for PZ26 material should be at 2 mm along the radial direction, or thickness for a 4 MHz transducer for PZ26 material should be at 0.5 mm along the radial direction.

The frequency content of the electric drive signal can be obtained directly, in case of a simple alternating voltage having one frequency, such as a pure sinusoidal signal. It can also be obtained through Fast Fourier Transform (FFT), as known to the man skilled in the art of signal processing.

It can be noted that, the intensity/power of the ultrasound field generated by a given transducer will depend on the amplitude of the electric drive signal delivered by the generator 10 at the operating frequency.

The implantable device 12 has articulating portions along the active portion on the elongation path 11, so that it can deform, i.e. adapt its shape, to a curved elongation path 11.

As whole, the implantable device 12 is thus flexible along at least part of the length of its active portion in order to be insertable in the spinal canal. This involves following the curved shape of the spinal canal along the elongation of the spine. This also involves allowing the insertion of the implantable device 12 through a primary access vertebra from an opening.

Indeed the implantation of the implantable device 12 is to be performed either by a surgical process, involving a surgical opening, or by a percutaneous process, involving a much smaller percutaneous opening. In both cases, the opening is preferably practiced in the spine region of the back of the patient. A distal end 21 of the device, here of the elongate tube 22, is introduced though the surgical or percutaneous opening and is guided towards the spinal canal portion of the primary access vertebra, passing between said vertebra and a proximal vertebra, for example between respective laminas of the two vertebras. The distal end 21 of the implantable device 12 is then guided along the spinal canal, in the subdural and/or in the epidural space, for example following a front or rear surface of the spinal cord.

The insertion process can be performed blindly, but it is preferably monitored by known imaging techniques, including X-Ray or ultrasound imaging techniques, including by endoscopy.

The flexibility of the device 12 along its elongation path 11, at least along its active portion, should allow this insertion and this ability to follow the shape of the spinal canal. The skilled practitioner will be able to determine the required flexibility to avoid any damage to the tissues, especially to the spinal cord and especially during the insertion process.

According to a desirable feature deriving from that flexibility, the implantable device 12 as a whole, including its elongate support member 22, 32, its transducers and its electrical connection circuits(s) in the active portion, is preferably at least manually deformable between at least a first spatial configuration, or shape, to at least a second spatial configuration or shape, meaning that, before its implantation or during its implantation, the implantable device 12 may be deformed to a desired shape by the mere application of biasing or deformation forces which are comparable to those which may be easily applied by hand. Typically, for an implantable device 12 to be considered as flexible, a surgeon implanting such device should be able to deform the implantable device 12 to give it a certain spatial configuration without resort to any kind of tool. This does not prevent however that deformation and/or implantation of the implantable device 12 can be deformed/implanted using tools typically employed in surgery, especially tools for performing remote-control surgery.

Preferably, the implantable device 12 is reversibly deformable such that, after it has been deformed from a first spatial configuration to a second spatial configuration, it can be deformed back to its first spatial configuration or very near to such spatial configuration.

The amount of manual reversible deformation possible for a given implantable device may be evaluated as a curvature radius of the elongation path. Preferably, the implantable device is reversibly deformable such that its elongation path may exhibit, along the active portion of the device and after reversible deformation, a radius of curvature of less than 15 cm, preferably less than 10 cm.

The implantable device 12 as a whole, including its elongate support member 22, 32, its transducers and its electrical connection circuits(s) in the active portion, has preferably a low degree of elasticity. If the implantable device is deformed from an initial spatial configuration to a temporary spatial configuration upon application of a biasing or deformation force, it may attain a final spatial configuration, due to a spring back effect, upon release of the biasing or deformation force. Low elasticity can be assumed if the difference of radius of curvature of the final spatial configuration compared to the temporary spatial configuration (i.e. due to the spring back effect) is for example less than one fourth of the radius of curvature of the temporary spatial configuration, preferably less than one tenth.

Preferably, the implantable device 12 as a whole, including its elongate support member 22, 32, its transducers and its electrical connection circuits(s) in the active portion, may be ultra-flexible, i.e. exhibiting a very low degree of rigidity. Such implantable device 12 cannot hold its own weight. For example, an implantable device 12 will be considered ultra-flexible if, along at least one test direction, when the implantable device 12 is clamped at one extremity of the active portion of the implantable device 12 so that the clamped extremity extends substantially horizontally, the implantable device 12 exhibits, by virtue of its sole weight, a radius of curvature of less than 15 cm along its active portion. Such an ultra-flexible implantable device 12 will have the advantage of generating the least possible pressure on the tissues which may be due to its deformation. Such ultra-flexible implantable device 12 may also be defined by the fact that it automatically adopts the shape of a surface it is in contact with, without generating any pressure, or at least without generating any substantial pressure, which pressure would be due to its own elasticity or rigidity. Of course, it may generate some pressure, for example due to its weight, and/or due to its thickness if sandwiched between two surfaces.

In some embodiments, one, several or all the articulating portions may comprise mechanical articulating portions comprising two rigid parts having a relative motion along respective sliding surfaces, such as a pivot or ball joint connection. For example, the support member may comprise a skeleton having successive rigid segments articulated one to the other by mechanical articulations.

An articulating portion may have three rotational degrees of freedom, as in a spherical ball joint.

An articulating portion may have two rotational degrees of freedom, or may have two preferred rotational degrees of freedom, for example around two axes perpendicular to the elongation axis with more limited flexibility or no rotational freedom of rotation along the third perpendicular axis, for example along the elongation axis.

However, an articulating portion may have only one rotational degree of freedom, or have one preferred rotational degree of freedom for example around an axis perpendicular to the elongation axis, with more limited or no rotational freedom of rotation along the elongation axis and along the other perpendicular axis.

A preferred rotational degrees of freedom is one for which the articulating portion of the device shows greater flexibility than for non-preferred rotational degrees of freedom.

As a whole, by proper choice of preferred rotational degree(s) of freedom of its successive articulating portions, an implantable device may exhibit a preferred plane of deformation, where the implantable device, as a whole, will exhibit greater flexibility along its active portion than for a non-preferred plane of deformation.

In all cases, an articulating portion may have a limited angular range of articulation for a one or several of its rotational degree of freedom. A limited angular range of articulation for one of its rotational degree of freedom may be different than a limited angular range of articulation for another rotational degree of freedom of a same articulating portion.

However, as shown in the depicted embodiment, an articulating portion of the device preferably comprises a flexible deformation portion 25. Such flexible deformation portions 25 are preferably part of the support member(s) which support the transducers. Typically, the flexible deformation portions 25 are part of support member 22, 32, i.e. of the distinct support member 22 and/or of the elongate tube 22.

In some embodiment, the implantable device 12 as a whole may exhibit a constant flexibility, at least along its active portion, or part thereof. In such a case, the articulating portions form a continuous articulating portion along the length of the implantable device 12, or at least along the length of its active portion, or part thereof.

In the example shown, articulating portions 25 are located along the elongation path between treatment transducers 22 along the elongation path 11.

The articulating portions may be formed of comparatively more flexible portions 25 of the device 12, in between of comparatively more rigid portions 27.

The comparatively more rigid portions 27 may correspond to the location of the treatment transducers 22 along the elongation path 11. Indeed, most ultrasonic treatment transducers 20 comprise a rigid core which generates the vibration. In an embodiment where the support member 22, 32 for the transducers is formed of a flexible material, such rigid transducers will impart a relatively high degree of rigidity to the corresponding portion of the device.

Accordingly, especially in such cases, it is preferable to provide a certain distance between two successive treatment transducers 20 along the elongation path 11. Such distance is for example superior to 5 mm, preferably superior to 10 mm.

Thus, a portion of the device, extending between two successive treatment transducers along the elongation path 11, may form an articulating portion 25, where the articulation is formed thanks to the flexible deformation of the support member 22, 32 along such portion.

This can also be provided when the support member 22, 32 comprises rigid segments which are articulated between each other, as this avoids mechanical interference between successive treatment transducers 20 upon curving of the shape of the implantable device.

Such distance between two treatment transducers 20 also limits the risk of the ultrasound waves generated by two successive transducers overlapping in the treatment zone. Such overlapping could indeed lead to undesired peak ultrasound power in the overlapping zone.

It can be noted that the support member 22, 32, on which the treatment transducers are affixed, remains in place within the implantable ultrasound generating device 12 when the latter is used, i.e. during application of the ultrasound treatment beam by activation of the ultrasound generating treatment transducers 20. This does not prevent that a removable mandrel may be used in connection with the implantable ultrasound generating device 12, especially during insertion of the device in the body of the patient. Such removable mandrel may comprise an inner mandrel which may be temporarily received within the implantable ultrasound generating device 12.

The implantable ultrasound generating treating device 12 may comprise ultrasonic monitoring transducers, for example wideband ultrasonic transducers. Monitoring transducers may comprise flexible membrane transducers. Monitoring transducers are preferably able to pick-up an ultrasound signal over a wide frequency range, ideally between 50 kHz and 50 MHz. Such monitoring transducers may be tailored and used for monitoring cavitation due to the ultrasonic treatment. The ultrasonic monitoring transducers may be held by the same support member as the treatment transducers, for example the elongate tube 22, or by a separate support member. One or several ultrasonic monitoring transducers may be located in between two treatment transducers.

The implantable ultrasound generating treating device 12 also comprises an electrical connection network for connecting the ultrasound generating transducers 20 to the generator 10 delivering electric drive signals. In the shown embodiment, the electrical connection network starts from the connection receiver 16 and delivers electric signals to the transducers for driving the ultrasound generation of the transducers. In some embodiments, an electric drive signal may serve both as power signal and as a control signal. The electric connection network may comprise one or several electrically independent electric connection circuits 24, where it will be understood that a given electric connection circuit 24 is a circuit where a common electric drive signal is circulating.

In some embodiments the electric connection network may comprise only one independent electric connection circuit 24 for the treatment transducers, so that the electric connection between implantable ultrasound generating device 12 and the generator, here through the connector 13 and the connection receiver 16, can be made as simple as possible. Indeed, in such a case, only one two-way connection will be needed for connecting the treatment transducers, with one electrical channel for the signal connection and one electrical channel for the ground return. Such a single electric connection circuit implies that all treatment transducers are driven by a single electric drive signal.

However, the electric connection network may comprise several independent electric connection circuits. An independent electric connection circuit may be used to drive a single treatment transducer or may be used to drive a group of treatment transducers. Each independent electric connection circuit will have its own independent electric connection to the generator 10 and the generator may deliver separate and different electric drive signals to each independent electric connection circuit. Independent electric connection circuit may be useful for addressing possible impedance variation between transducers.

In any case, monitoring transducers, if present, would preferably have their own separate electric connection circuit.

In the shown example, although it is implantable, the connection receiver 16 is separate from the elongate tube 22. Therefore, the electric connection circuit 24 comprises at least one cable 26, most commonly made of at least one pair of wires where one wire corresponds to one independent electrical channel, which extends outwardly from a proximal end 23 of the the elongate tube 22 to the connection receiver 16. Preferably, there is a single cable 26, although it may comprise several electrically separate wires bundled together. Inside the elongate tube 22, the cable 26 of electric connection circuit 24 may separate into connection lines 28 for delivering an electric drive signal to the individual transducers 20 of a given group of transducers.

The implantable device 12 may have, in cross section perpendicularly to its elongation axis, a shape where the outer surface, for example the outer surface of an outer protective sheath, is in the shape of, or aligned along a line which can be a circle or a part thereof such as a semi-circle, an ellipse or quasi ellipse or part thereof, a parabola or quasi parabola or part thereof, an hyperbola or quasi hyperbola or part thereof, or any curved or prismatic line. The shape of the implantable device 12 in cross section might be identical to that of the radial treatment transducers 20, or not.

Preferably, the implantable device 12, thus here the elongate tube 22, has a maximum transverse dimension perpendicular to its elongation path, for example its external diameter in the case of device of circular cross section, which is less than 6 mm, preferably less than 4 mm.

Preferably, the implantable ultrasound generating treating device 12 is made of non-ferromagnetic material, preferably MRI compatible material.

When designed to be connected to an external generator, the implantable ultrasound treating device 12 may be designed with an external, i.e. non-implantable, connection receiver 16.

In the case of an implantable connection receiver 16, the connection receiver 16 may have a casing, for example a rigid casing, which may be fastened to a vertebra by any suitable means, such as bone screws.

For example, one or several connecting plugs may be located within the implantable casing and may be adapted to physically connect with one or several connecting needle(s) 14 from the generator systems. A connecting needle 14 is preferably a transdermal needle. Such needles are suitable for piercing the patients skin and plugging into the connecting plugs inside the implantable casing, preferably through a wall of the casing which can be advantageously made of, or comprise a portion made of, an isolating concealable material like Silastic®, from the silicone manufacturer Dow Corning. This material can easily and automatically reseal when the needle 14 is withdrawn from the implantable connection receiver 16. Advantageously, the transdermal needle 14 may be coated with an isolating material, for instance wax or plastic, on its entire length except at its tip so that an electric contact can be established at its tip with a connecting plug inside the connection receiver to transfer electric current to the implantable connection receiver 16 without causing burning of the patient's skin. An embodiment may comprise a two-way connection by means of a single transdermal needle 16 which carries, on one way, i.e. one electrical channel, the electric drive signal and, on the other way, the ground connection between the generator 10 and the implantable treating device 12, which in this case, has only one independent electric connection circuit 24, thus only one group of transducers. Two single-way needles could have been provided, one for the electric drive signal and one for the ground return. Further description of such connection can be found in U.S. Pat. No. 8,977,361 which is hereby incorporated by reference.

However, in case of an implantable ultrasound generating device having several independent electrical connection circuits, an independent connection for each electrical signal corresponding to each independent electrical connection circuit would be needed, plus at least one common ground connection. This could be achieved with a single needle having one way per electrical signal plus one way for the ground return, or with several needles.

The generator 10 is adapted for delivering electric drive signals to be delivered to the ultrasound generating treatment transducers 20 of an associated ultrasound generating treating device 12. The generator typically comprises an alternating voltage generator able to generate an electric signal, for example a sinusoidal electric voltage signal. One example of a generator system that can be used with the inventive device may include a system that integrates signal generation, amplification, and control into a single unit. However, a generator system can also comprise one or several individual components performing one or more of these functions. For example, the generator can include an HP/Agilent 33120 function generator. If needed, it can also include for example one or more of an ENI 240L Broadband RF amplifier, of a Rhode and Schwarz RF power meter, and/or external computer controlling equipment over GPIB/Serial/USB interfaces.

Therefore, the controller 15 may comprise a computer. A computer human/machine interface 17, for example a keyboard, and/or mouse and/or a display and/or a touchscreen interface, can be provided to control the system and give the user feedback. A radiofrequency board that generates the RF signal and amplifies it may be provided, as well as a coupler to measure the delivered RF power, and matching components to tune the generator output to the impedance of the ultrasound elements. Preferably, the generator 10 may be of a type capable to deliver 25-100 W peak RF power, capable of sending burst lengths with durations of 1 microsecond to continuous mode, and capable of sending bursts within the frequency range of 500 kHz to 2 MHz. Such a system can be controlled to send pulses with variable frequency and duty cycles for durations of approximately 2-5 minutes. The generator may be a class A/B RF system, which means that it is capable of generating nearly pure sinusoidal signals, but this may make the system rather large. In some embodiments, especially in the case where the generator is implantable, the generator could be a class D system, which tends to generate signals that are square wave on the output.

The controller 15 may thus comprise a treatment control module for controlling the generator of view of providing the adequate electric drive signals to the implantable ultrasound treating device 12.

The controller 15 may also comprise a monitoring module connected to the monitoring transducers of the implantable ultrasound treating device 12, if provided with such monitoring transducers.

According to another aspect of the invention, it is provided a method for transiently opening the blood-spinal cord barrier (BSCB) or blood-spinal nerve barrier (BSNB) in at least one treatment zone of the spinal cord or spinal nerve(s) of a vertebrate patient, especially of a human patient.

In the context of the invention, the terms "disrupting", "opening" or "increasing the permeability" of the BSCB or BSNB are used interchangeably to refer to an increased susceptibility of the BSCB or BSNB to the passage of molecules therethrough that occurs without detectable damaging of the spinal cord or spinal nerve tissue.

The method can be used for delivering substances into targeted spinal cord or spinal nerve tissue of the subject and/or for treating a the spinal cord or spinal nerve disease.

The method comprises the application to the treatment zone of the spinal cord of the patient of at least one ultrasound treatment beam.

The terms "ultrasound beam", "ultrasound wave" and "ultrasound" are used indifferently for designating sound waves with frequencies higher than 20 kHz. However the ultrasound treatment beam has preferably an ultrasound frequency ranging from 0.5 to 4 MHz, more preferably ranging 0.75 to 2 MHz.

The ultrasound energy may be focused ultrasound or unfocused ultrasound to treat a large zone of the BSCB or BSNB.

The method comprises the insertion of an implantable ultrasound generating treating device inside the spinal canal of the spine of the patient and the generation of least one ultrasound treatment beam. The use of such an implantable device allows for a very precise control of the ultrasound energy and power delivered to the targeted spinal cord and spinal nerve tissues. It also allows a precise targeting of the treatment zone, with the possibility to precisely control the extension of such treatment zone where the ultrasound treatment beam is effectively applied.

Most preferably the implantable ultrasound generating treating device is implanted in the subdural and/or in the epidural space of the spinal canal.

The implantable ultrasound generating treating device 12 may be maintained in the spinal canal of the patient for days, weeks or months. It is then possible to perform repetitive BSCB or BSNB disruptions for a long period of time. The implantable ultrasound generating treating may be activated for each BSCB or BSNB disruption, for instance before each chemotherapy session of a patient in need thereof.

In the context of the invention, a "transient" opening refers to a reversible opening occurring preferably for more than 1 hour, the BSCB or BSNB returning after that to its initial state (i.e., the BSCB or BSNB state before the application of the first ultrasound treatment beam).

In some embodiments, the BSCB or BSNB opening occurs for a period of time from 1 to 48 hours, preferably from 5 to 24 hours, more preferably from 6 to 10 hours. In some embodiments, the BSCB or BSNB opening occurs for approximately 8 hours.

In some embodiments, the BSCB or BSNB disruption is delimited, i.e., occurs solely in a target region of the BSCB or BSNB. For instance, only a region of the BSCB or BSNB surrounding damaged spinal cord or spinal nerve tissue, such as a tumor, is targeted. In other embodiments, the BSCB or BSNB disruption is generalized.

The disruption may be easily confirmed and/or evaluated by magnetic resonance imaging (MRI). For example, a gadolinium-based magnetic resonance (MR) contrast agent such as Dotarem® (gadoterate meglumine, Guerbet USA), which does not normally cross the BSCB or BSNB, can be used to visualize the region of BSCB or BSNB disruption. When the agent is injected in a patient, a T1w MR sequence can be used to visualize regions of hypersignal and therefore visualize the effect of BSCB or BSNB disruption by ultrasound. BSCB or BSNB disruption typically leads to a change of 5-10% or more in MR signal enhancement after contrast agent administration. With the invention, a change of more than 25%, preferably more than 50% in MR signal enhancement after contrast agent administration is contemplated. In addition, dynamic contrast enhanced (DCE) MR imaging techniques can be used to calculate the permeability of the BSCB or BSNB and to quantify the magnitude of the permeability enhancement after ultrasound treatment.

The treatment zone can be very limited in its extension, for example corresponding to the spinal canal portion of a single vertebra. However, the treatment zone may extend throughout the extension of several vertebrae of the patient. In such a case the method may comprise the insertion of an elongate implantable ultrasound generating treating device inside the spinal canal of the spine and the generation of least one ultrasound treatment beam. In the case of an adult human, the length of the active portion on an elongate implantable ultrasound generating transducer is preferably of at least 10 cm, preferably at least 20 cm and more preferably at least 40 cm The method preferably involves the injection of an ultrasound contrast agent in the patient's blood circulation system, prior to and/or during the generation of the least one ultrasound treatment beam.

The term "ultrasound contrast agent" is used herein to refer to a substance (solid, liquid or gas) that is able to enhance the contrast between the region containing the agent and the surrounding tissue in an ultrasound image. Advantageously, the ultrasound contrast agent corresponds to small bubbles of a gas, termed "microbubbles," with an average diameter between 1 µm and 10 µm. Said microbubbles oscillate and vibrate when a treatment ultrasound beam is applied and may reflect ultrasound waves. The ultrasound contrast agent is generally injected intravenously into the blood stream in the patient's blood circulation system, wherein it remains for a limited period of time.

The ultrasound contrast agent may be administered by injection, preferably by systemic injection. Examples of systemic injections include intravenous, subcutaneous, intramuscular, intradermal, intra vitreal and intraperitoneal injection, or perfusion.

Preferably, the ultrasound contrast agent is administered as a bolus just before the ultrasound treatment beam application. More preferably, the ultrasound contrast agent is administered between 0 and 60 minutes before, and/or during the ultrasound treatment beam application. When successive ultrasound treatment beams are applied, the ultrasound contrast agent is preferably delivered only once, just before the first ultrasound treatment beam application of the cycle, though it may be delivered at activation of each US beam, or by a continuous infusion through the activation of successive ultrasound treatment beams.

According to the invention, the ultrasound contrast agent may contain gaseous bubbles, a high concentration of gas, solid particles configured to vaporize in response to ultrasound, liquid configured to vaporize in response to ultrasound, micro particles configured to act as cavitation sites, solid particles having higher acoustic impedance than tissue in the desired region, and/or liquid with a high acoustic absorption coefficient.

In some embodiments, the ultrasound contrast agent is a microbubble contrast agent, preferably selected from the group consisting of sulphur hexafluoride microbubbles (SonoVue®), microbubbles made of an albumin shell and octafluoropropane gas core (Optison®), perflexane microbubbles encapsulated in an outer lipid shell (Imagent®), microbubbles made of octafluoropropane gas core encapsulated in an outer lipid shell (Definity®), or perfluorobutaine and nitrogen gas encapsulated in a lipid shell (BR38—Schneider et al., 2011). Preferably, the ultrasound contrast agent consists of sulphur hexafluoride microbubbles. Microbubbles may contain a drug and/or a nanoparticle which may be delivered in situ when the microbubbles are exposed to the ultrasound treatment beam.

The microbubbles may have a mean diameter in a range from 1 µm to 10 µm. In some embodiments, the microbubbles have a mean diameter in a range from 4 µm to 5 µm. In some other embodiments, the microbubbles have a mean diameter in a range from 2 to 6 µm. In some embodiments, the microbubbles have a mean diameter of approximately 7 µm, 6 µm, 5 µm, 4 µm, 3 µm or 2 µm. In a particular embodiment, the microbubbles have a mean diameter of approximately 2.5 µm.

In some embodiments, the dose of ultrasound contrast agent ranges between 0.05 and 0.15 ml/kg based on the total weight of the subject. Preferably, the dose of ultrasound contrast agent is approximately 0.1 ml/kg. In a particular embodiment, the maximum dose of ultrasound contrast agent is up to 10 ml.

Preferably, the pressure level of the ultrasound treatment beam applied to the spinal cord or spinal nerve tissues is comprised between 0.8 MPa and 3.0 MPa. Advantageously, the ultrasound treatment beams are applied within a pressure range of 0.8 MPa to 2.5 MPa, more preferably within a pressure range of 0.8 MPa to 2.00, even more preferably within a pressure range of 0.8 MPa to 1.9, such as within a pressure range of 0.8 MPa to 1.5 MPa, within a pressure range of 1.1 MPa to 1.5 MPa. In a particular embodiment, the ultrasound treatment beams are applied with a pressure level of 1.25 MPa. In another embodiment, the ultrasound treatment beams are applied with a pressure level of 1.5 MPa. In a further embodiment, the ultrasound treatment beams are applied with a pressure level of 1.9 MPa. In the context of the invention, the "pressure level" refers to the maximum acoustic pressure measured in the acoustic field of the device in water. It is believed that such pressure levels may be applied in a safe manner to human's spinal cord and/or spinal nerve, i.e., no detected damages of spinal cord and/or spinal nerve tissue should be observed.

In the context of the invention, the value of the pressure level corresponds to the value onto the spinal cord and/or spinal nerve tissue. The pressure emitted by the device may differ, to take into account potential attenuation of intervening tissues and/or vertebra bone reverberation. One skilled in the art will be able to adapt the value of the pressure level coming out of the emitter to obtain the required pressure level onto the spinal cord and/or spinal nerve. Monitoring of the treatment zone with ultrasonic monitoring transducers can be used for checking the effective value of the pressure level in situ during the treatment. Monitoring of the treatment zone with ultrasonic monitoring transducers can be used to record emitted ultrasound signal (harmonics, subharmonic waves, all broad band emission frequencies waves) from microbubbles during their cavitation induced by therapeutic transducers. This echo detected signal can allow the monitoring of inertial or stable cavitation of the microbubbles.

Preferably, the applied ultrasound treatment beam has a mechanical index (MI) of approximately from 0.3 to 3.00, and preferably in the range of 1.05 to 1.8 in the case of a 1 MHz ultrasound treatment beam. In the context of the invention, the MI refers to the peak negative pressure in situ (MPa) divided by the square root of the frequency (MHz).

Preferably, the ultrasound treatment beam is a pulsed beam. In the context of the invention, a "pulse" refers to a continuous burst, without interruption, of sinusoidal waves that may comprises several cycles.

In some embodiments, the method comprises the application of one or more pulses, or bursts, comprising from 100 to 100,000 successive cycles, preferably from 1,000 to 75,000, more preferably from 10,000 to 50,000, even more preferably from 20,000 to 30,000. In a particular embodiment, the method comprises the application of pulses of 25,000 successive cycles. In some embodiments, the mean burst duration of an ultrasound treatment emission (i.e., the mean time from the start of a pulse to the end of that pulse) is between 10 msec. and 100 msec., preferably between 15 msec. and 50 msec., more preferably between 20 msec. and 30 msec., even more preferably approximately 25 msec.

The delay between two successive pulses is preferably from 30 msec. to 1000 msec. In a particular embodiment, the delay between two successive pulses is approximately 975 msec.

Advantageously, the successive pulses are applied within a total duration from 1 to 20 minutes. In a particular embodiment, the successive pulses are applied within a total duration that does not exceed 10 minutes, preferably 5 minutes. In a particular embodiment, the successive pulses are applied within a total duration of 150 seconds.

In a particular embodiment, pulses of 25,000 cycles are applied to the subject, at a pulse repetition frequency (PRF) of 1 Hz, every 1000 msec. with a pressure level of 1.1 MPa and a burst duration of about 23 msec. for a total duration of 150 seconds.

A treatment transducer has an ultrasound emission zone in which the intensity of the ultrasound field is significant. The ultrasound emission zone can be defined by a border emission envelope of the emission zone which can itself be defined as the envelope containing all locations where the acoustic pressure of the ultrasound field is equal to at least a certain percentage, for example 25%, of the acoustic pressure at the same distance from the transducer along a direction of maximum acoustic pressure. As discussed above, the treatment transducers 20 of an implantable device according to the invention are preferably designed and arranged along the support member 22, 32 so the emission zones of two successive treatment transducers along the elongation path 11 do not intersect. Providing two successive treatment transducers 20 at a certain distance from each other, as described above, for example at least 10 mm apart, participates in avoiding such intersection However, as a complement or an alternative, it can be provided that two successive treatment transducers 20 are not activated simultaneously.

For example, the treatment transducers 20 can be divided in two or more sets of non-consecutive treatment transducers 20 along the elongation path 11, each set of treatment transducers being activated separately in time, not simultaneously. For example, one can provide two or three sets of transducers 20, where each set is made of one out of every two treatment transducers 20, respectively one out of every three treatment transducers 20, along the elongation path 11.

Each set of treatment transducers, which is to be activated separately in time, may be electrically connected to the generator through its own independent electrical connection circuit.

The method according to the invention is preferably implemented with the use of an implantable ultrasound generating treating device as described above, and preferably with a treatment apparatus comprising such a device.

The devices, apparatus and methods according to the invention can be used to treat various physiological disorders which induce different forms of pathologies including;
- spinal degenerative pathologies, such as amyotrophic lateral sclerosis (ALS);
- spinal cord tumor diseases, such as spinal astrocytomas;
- spinal inflammatory pathologies, such as multiple sclerosis, etc . . . .

It can also be used to improve the repair and/or rehabilitation treatments of the spinal cord and/or spinal nerve(s), for example for hemiplegia and paraplegia, including with cell transplant and/or stem cell regeneration.

The invention claimed is:

1. A method for transiently opening the blood-spinal cord barrier in at least one treatment zone of the spinal cord of a vertebrate patient, said method comprising:
    applying, to the at least one treatment zone of the spinal cord of the patient, at least one ultrasound treatment beam, wherein the applying step further comprises inserting an implantable ultrasound generating treating device inside subdural and/or in an epidural space the spinal canal of the spine of the patient and generating the at least one ultrasound treatment beam,
    wherein the method includes injecting of an ultrasound contrast agent in a blood circulation system of the patient, prior to and/or during the generation of the least one ultrasound treatment beam,
    wherein the at least one ultrasound treatment beam is a pulsed beam having a mean burst duration, a mean time from a start of a pulse to an end of that pulse is between 10 msec. and 100 msec., and a delay between two successive pulses is from 30 msec. to 1000 msec,
    wherein the at least one ultrasound treatment beam has a resonant frequency ranging from 0.5 to 4 MHz,
    wherein the pressure level of the at least one ultrasound treatment beam is between 0.8 MPa and 3.0 MPa,
    wherein the at least one treatment zone extends throughout an extension of several vertebrae of the patient, and
    wherein the implantable ultrasound generating treating device is an elongate implantable ultrasound generating treating device sized to extend throughout the extension of the several vertebrae.

2. The method according to claim 1, wherein the applied ultrasound treatment beam has a mechanical index of from approximately 0.3 to 3.00.

3. The method according to claim 1, wherein the implantable ultrasound generating treating device comprises:
    an elongate support member extending along an elongation path;
    an array of several ultrasound generating treatment transducers distributed along the elongate support member along an active portion on the elongation path;
    wherein the several treatment transducers comprise radial treatment transducers, each radial treatment transducer emitting an ultrasound treatment beam oriented radially with respect to the elongation path over an effective angular range of at least 120° around the elongation path at the location of the radial treatment transducer;
    wherein the radial treatment transducers have an ultrasound generating resonant frequency comprised between 0.5 and 4 MHz, and
    wherein the device has articulating portions along the active portion of the elongation path so that the active portion of the implantable ultrasound generating device can adapt its shape to a curved elongation path.

4. The method according to claim 3, wherein two successive radial treatment transducers are provided at a distance apart from each other of at least 10 mm.

5. A method for transiently opening the blood-spinal cord barrier in at least one treatment zone of the spinal cord of a vertebrate patient, said method comprising:

applying, to the at least one treatment zone of the spinal cord of the patient, at least one ultrasound treatment beam, wherein the applying step further comprises inserting an implantable ultrasound generating treating device inside subdural and/or in an epidural space the spinal canal of the spine of the patient and generating the at least one ultrasound treatment beam, wherein the method includes injecting of an ultrasound contrast agent in a blood circulation system of the patient, prior to and/or during the generation of the least one ultrasound treatment beam, wherein the at least one treatment zone extends throughout an extension of several vertebrae of the patient, and wherein the implantable ultrasound generating treating device is an elongate implantable ultrasound generating treating device sized to extend throughout the extension of the several vertebrae.

6. The method according to claim 5, wherein the applied ultrasound treatment beam has a mechanical index of from approximately 0.3 to 3.00.

7. The method according to claim 5, wherein the implantable ultrasound generating treating device comprises:

an elongate support member extending along an elongation path;

an array of several ultrasound generating treatment transducers distributed along the elongate support member along an active portion on the elongation path;

wherein the several treatment transducers comprise radial treatment transducers, each radial treatment transducer emitting an ultrasound treatment beam oriented radially with respect to the elongation path over an effective angular range of at least 120° around the elongation path at the location of the radial treatment transducer;

wherein the radial treatment transducers have an ultrasound generating resonant frequency comprised between 0.5 and 4 MHz, and wherein the device has articulating portions along the active portion of the elongation path so that the active portion of the implantable ultrasound generating device can adapt its shape to a curved elongation path.

8. The method according to claim 7, wherein two successive radial treatment transducers are provided at a distance apart from each other of at least 10 mm.

9. The method according to claim 5, wherein the at least one ultrasound treatment beam is a pulsed beam having a mean burst duration, a mean time from a start of a pulse to an end of that pulse is between 10 msec. and 100 msec., and a delay between two successive pulses is from 30 msec. to 1000 msec.

10. The method according to claim 5, wherein the at least one ultrasound treatment beam has a resonant frequency ranging from 0.5 to 4 MHz.

11. The method according to claim 5, wherein the pressure level of the at least one ultrasound treatment beam is between 0.8 MPa and 3.0 MPa.

\* \* \* \* \*